United States Patent [19]

Bekierkunst et al.

[11] 4,340,586
[45] Jul. 20, 1982

[54] PHARMACEUTICAL PREPARATION FOR TREATING DISORDERS OF THE SKIN

[76] Inventors: Adam Bekierkunst; Haim A. Cohen, both of Alcharisi 21, Jerusalem, Israel

[21] Appl. No.: 769,960

[22] Filed: Feb. 18, 1977

[51] Int. Cl.$^3$ ............................................. A61K 39/02
[52] U.S. Cl. .................................................... 424/92
[58] Field of Search ......................................... 424/92

[56] References Cited

FOREIGN PATENT DOCUMENTS 1128005  9/1968  United Kingdom ................. 424/92

OTHER PUBLICATIONS

Bekierkunst et al., Inffct. Immunity, 10, pp. 1044–1050 (1974).
Bekierkunst, A., Int. J. Cancer 16 (1975), pp. 442–447.

*Primary Examiner*—Jerome D. Goldberg
*Attorney, Agent, or Firm*—Browdy and Neimark

[57] ABSTRACT

A pharmaceutical preparation for topical application, for the treatment of disorders of the skin, comprising killed mycobacteriae in a suitable vehicle, advantageously in combination with cord factor (CF) and a method for the treatment of disorders of the skin of mammals and especially humans, including premalignant and malignant types of growth and of conditions due to the immunodeficiency of the mammal treated, which comprises disinfecting the affected area of the skin, removing the stratum corneum (horny layer) by repeated application of adhesive tape and applying thereto an ointment as defined above, covering same with an impervious wrap and leaving same in place for 1 to 2 days, and if necessary repeating the treatment at suitable intervals of time.

3 Claims, No Drawings

PHARMACEUTICAL PREPARATION FOR TREATING DISORDERS OF THE SKIN

FIELD OF THE INVENTION

The invention relates to an ointment for the treatment of diseases of the skin. More particularly it relates to an ointment and process for the treatment of the skin. Other and further aspect will become apparent hereinafter.

BACKGROUND OF THE INVENTION

The prior art indicates that Guinea pigs with transplanted hepatocellular carcinoma (Line 10) in their skin and metastases in their regional lymph nodes can be cured by the intralesional injection of living BCG (see Zbar et al., Science 172 (1971) 271-3). Killed BCG or BCG cell walls suspended in saline are not therapeutic in this system. Cures comparable to those produced by living BCG have been produced by the intralesional injection of BCG cell wall fragments attached to mineral oil which was emulsified in an aqueous solution of saline containing Tween 80. One of the components of the mycobacterial cell wall is cord factor (trehalose-6,6-dimycolate), (see Lederer, Pure Appl. Chem. 25 (1971) 135-150), a compound which possesses some of the biological properties of living BCG. Cord factor suppresses the development of urethane induced tumors in the lungs of mice to an extent similar to that produced by living BCG (Bekierkunst, A., et al. Science 174 (1971) 1270. It was found that a mixture of delipidated and deproteinized cell walls from Mycobacterium tuberculosis H37Ra suspended in 1.25% mineral oil emulsion cured established tumours in the skin after intratumoural administration in 33% of the cases. This was increased to 83% when a mixture of cord factor and delipidated cell walls was used (Bekierkunst A. et al, Infection and Immunity, 10 (1974) 1044).

A similar percentage of cures was obtained with heat-killed BCG cells coated with cord factor. This compares favorably with the rate of cure achieved with living BCG cells (about 60%). A vaccine containing dead BCG and living tumor cells prevented the growth of tumor cells introduced distally into the skin of guinea pigs at the time of vaccination. The efficacy of the vaccination was substantially increased when cord factor was included in the vaccine (Bekierhunst A., Int. J. Cancer, 16 (1975) 442).

SUMMARY OF THE INVENTION

The present invention relates to a novel pharmaceutical preparation for topical application, adapted to treat and cure certain types of disorders of the skin. The invention also relates to a method of treatment of certain disorders of the skin of mammals, and especially of humans, by means of the novel pharmaceutical preparations of the present invention.

Amongst disorders of the skin which can be effectively treated by means of the ointments according to the present invention are those of the group consisting of mycosis fungoides, basal cell carcinoma, keratosis solaris, Bowen squamous cell carcinoma, Kaposi sarcoma, leishmaniasis diffusa, adenocarcinoma and melanoma. Experiments carried out with patients affected with the above diseases have shown that a high percentage of cures can be attained by topical application of the novel ointment.

The active ingredients of the novel ointment are killed bacteria of the mycobacteriaceae type, that is BCG, advantageously in combination with cord factor (CF) i.e. trihalose 6,6-dimycolate. The active ingredient is provided in a suitable vehicle, as will be described in greater detail hereinafter.

Best results are obtained by the combination of mycobacteriae with cord factor, but mycobacteriae by themselves in higher quantities also give satisfactory results.

The bacteriae are killed, advantageously by heat, and lyophilized. Other methods of killing the bacteria and of their preparation can be used.

Hitherto experiments have shown the efficacy of BCG and of cord factor in the form of injections. This combination has been shown to be effective in the form of injections against various types of malignancies. It was thought that this is the only possible form of application, and thus this form was used in spite of all the unpleasant shortcomings and drawbacks. It was thought that only injections would be effective as it was believed that topical applications would not be effective due to the fact that bacteriae would not be able to penetrate the skin and exert the necessary activity at some depth. In view of this, it is quite unexpected and surprising that mycobacteriae, if desired in combination with cord factor, can be used in a suitable carrier for topical applications giving the desired results and high percentage of cures.

Any suitable inert vehicle adapted to efficiently maintain the active ingredients at the desired location can be used. Amongst suitable carriers there may be mentioned petroleum jelly (vaseline), organic and inorganic waxes, certain vegetable oils, carboxymethyl cellulose, aqueous base ointments, water in oil emulsions, and the like. Very good results were obtained with vaseline and with certain oils such as peanut oil.

The invention is illustrated in the following with reference to BCG (Bacillus Calmette Guerin), but it ought to be understood that other mycobacteriae of the types defined above can be used instead. The bacteriae are advantageously used in quantities of about 1.5 mg to about 15 mg killed bacteriae per gram of ointment in the case of BCG, in combination with about 0.07 mg to 0.15 mg cord factor per gram of ointment. The cultivation of mycobacteriae and their preparation in lyophilized state is described in literature. This applies also to the preparation of the cord factor. The ointments are advantageously prepared as follows: A weighed quantity of cord factor is inserted into a glass homogenizer and dissolved in ether. A weighed quantity of killed bacteriae, such as killed lyophilized BCG is added and the ether is evaporated. This results in the adherance of the cord factor, which is a glycolipid, to the lypophilic surface of the bacteriae. The cord factor coated bacilli are homogenized and dispersed in a suitable carrier such as liquified vaseline. After solidification of the carrier, the ointment is ready for use. Various ointments were prepared, containing from 1.5 mg per gram of ointment. The ratio of cord factor to bacilli is about 1:20 to 1:10. When only mycobacteriae are used, the quantity used is typically about 7.5 mg to 75 mg per gram in the case of killed and lyophilized BCG.

In order to use the ointment for the treatment of various types of skin diseases, of the types defined above, the affected and adjacent areas are first cleaned with 2% iodine or 70% ethanol or with any equivalent disinfecting agent. After disinfection the stratum corneum (horny layer) is stripped off by repeated application of Scotch tape. Usually 30 strippings are carried out. The ointment is applied to the stripped area and covered with an inert wrap, such as Saran wrap, and fixed in place with adhesive tape. It is left in place for about 48 hours. This results in an inflammatory cellular reaction at the site of the application which is associated with a mild transient systemic reaction in the form of chills and low fever in some cases. The application of the ointment is repeated at weekly or biweekly intervals, depending on the local and general reaction of the patient. The treatment described above resulted in the resolution of lesions in premalignant, infiltrative and tumor stages of mycosis fungoides; in the resolution of nodular and plaque lesions of sarcoma kaposi; in the resolution of basiliomas and lesions of keratosis solaris. This was attained by treating affected areas of the skin of the patient with the ointment according to the present invention.

The novel ointment for use as topical application is characterized by certain specific advantages compared with other pharmaceutical compositions of matter for similar purposes. Living BCG used in the form of injections cause sometimes diseminated disease in immunorepressed hosts and local reaction at the site of the injections may be severe. Deaths from generalized infection have been reported during large scale vaccinations. Many adverse effects due to the use of live BCG have been reported (see Laucius et al., J. Reticuloendothelial Soc. 16 (1974) 347 and Bast et al., New Engl.J.Med. 1974, 1413-20 and 1458-69). It is clear that live BCG cannot be used in the treatment of large affected areas of skin.

Five out of five cases of sarcoma kaposi; four out of four cases of premalignant stages of mycosis fungoides; two out of two cases of infiltrative stage of mycosis fungoides (malignant stage); one case of basilioma; two cases of solar keratosis; one case of a small squameous cell carcinoma were treated and cured; the only case of Leishmaniasis diffusa encountered was treated and cured by means of the ointment according to the present invention containing killed lyophilized BCG and cord factor. Preliminary results indicate that higher quantities of BCG by itself and also similar compositions of other types of mycobacteriaceae, of the species defined above, give satisfactory results in the treatment of disorders of the skin of the types defined above.

We claim:

1. A method for the treatment of a disorder of the skin of a human or other mammal selected from the group consisting of mycosis fungoids, basal cell carcinoma, keratosis solaris, Bowen squamous cell carcinoma, Kaposi sarcoma, leishmaniasis diffusa, adenocarcinoma and melanoma, which comprises disinfecting the affected area and adjacent areas of the skin, removing the stratum corneum by repeated applications of pressure sensitive type, applying an effective amount of ointment, consisting essentially of an amount sufficient of killed mycobacteriae BCG and cord factor (trehalose-6,6-dimycolate) to effectively treat mycosis fungoids, basal cell carcinoma, Kaposi sarcoma, leishmaniasis diffusa, adenocarcinoma and melanoma, in a vehicle suitable for topical pharmaceutical application and capable of efficiently maintaining the active ingredients at the desired location on the skin for 24 to about 48 hours, said amount sufficient of the active ingredients constituting from 1.5 mg to 75 mg per gram of said ointment of said killed mycobacteriae and from 0.07 mg to 0.15 mg of said cord factor per gram of ointment, covering same with an impervious wrap, and leaving same in place for a period of time of about 24 to 48 hours.

2. A method for the treatment of a disorder of the skin of a human or other mammal selected from the group consisting of mycosis fungoids, basal cell carcinoma, keratosis solaris, Bowen squamous cell carcinoma, Kaposi sarcoma, leishmaniasis diffusa, adenocarcinoma and melanoma, which comprises disinfecting the affected area and adjacent areas of the skin, removing the stratum corneum by repeated applications of pressure sensitive tape, applying an effective amount of an ointment, consisting essentially of an amount sufficient of killed mycobacteriae BCG and cord factor (trehalose-6,6-dimycolate) to effectively treat mycosis fungoids, basal cell carcinoma, Kaposi sarcoma, leishmaniasis diffusa, adenocarcinoma and melanoma, in a vehicle suitable for topical pharmaceutical application and capable of efficiently maintaining the active ingredients at the desired location on the skin for 24 to about 48 hours, said amount sufficient of the active ingredients constituting from 1.5 mg to 15 mg per gram of said ointment of said killed mycobacteriae and from 0.07 mg to 0.15 mg of said cord factor per gram of ointment, and said inert vehicle is selected from the group consisting of petroleum jelly, organic or inorganic waxes and peanut oil, covering same with an impervious wrap, and leaving same in place for a period of time of about 24 to 48 hours.

3. A method in accordance with claim 2, comprising repeating the treatment a number of times at intervals of a few days.

* * * * *